United States Patent [19]

Elango

[11] Patent Number: 5,012,007
[45] Date of Patent: Apr. 30, 1991

[54] METHOD FOR PRODUCING 1-INDANONE DERIVATIVES

[76] Inventor: Varadaraj Elango, 4175 Crenshaw Dr., Corpus Christi, Tex. 78413

[21] Appl. No.: 417,376

[22] Filed: Oct. 5, 1989

[51] Int. Cl.$^5$ .............................................. C07C 45/49
[52] U.S. Cl. ................................... 508/311; 564/428; 568/42; 568/43; 568/814
[58] Field of Search .................. 568/311, 814, 42, 43; 564/428

[56] References Cited

U.S. PATENT DOCUMENTS 3,466,332  9/1969  Bruson et al. .................. 568/311
3,466,333  9/1969  Bruson et al. .................. 568/311

FOREIGN PATENT DOCUMENTS 49-10949  3/1974  Japan .................. 562/406
55-27147  2/1980  Japan .................. 562/406
63-2942   1/1988  Japan .................. 568/311
63-2943   1/1988  Japan .................. 568/311

OTHER PUBLICATIONS

Warrick et al., J.A.C.S., vol. 84, pp. 4094–4100 (1962).
Nightingale et al., J. Org. Chem., vol. 14, pp. 1089–1093 (1949).

Primary Examiner—James H. Reamer
Attorney, Agent, or Firm—Donald R. Cassady; Marvin Turken

[57] ABSTRACT

A method is provided for the production of 2,2-diorgano-1-indanones, e.g., 2,2-dimethyl-1-indanone, by reacting an alcohol which is the corresponding (diorganosubstitutedmethyl)phenyl(or substitutedphenyl)carbinol, e.g., 2-methyl-1-phenyl-1-propanol, with carbon monoxide in the presence of a Lewis acid catalyst, e.g., hydrogen fluoride, with any substituents on the phenyl group of the alcohol being hydroxy or organo. The foregoing reaction is preferably integrated with the preparation of the feed alcohol by reducing the corresponding (diorganosubstitutedmethyl)phenyl(or substitutedphenyl)ketone, e.g., isobutyrophenone, with a reducing agent containing available hydrogen, e.g., sodium borohydride, or with hydrogen gas in the presence of a hydrogenation catalyst.

17 Claims, No Drawings

METHOD FOR PRODUCING 1-INDANONE DERIVATIVES

BACKGROUND OF THE INVENTION

1. Field of the Invention

This invention relates to a new method for the production of certain 2,2-diorgano-1-indanones. Various indanones of this class such as 2,2-dimethyl-1-indanone and 2,2-diethyl-1-indanone are valuable intermediates in the production of pharmaceuticals. For example, 2,2-dimethyl-1-indanone is used in the synthesis of the antiallergic agent 4-(6'-chloro-2',2'-dimethylinden-1'-ylidene)-1-methylpiperidine, the anti-inflammatory and antiarthritic 2,2-dimethylindane-5-acetic acid, and other bioactive compounds such as coumarins.

2. Description of Related Art

The following information is disclosed in accordance with the terms of 37 CFR 1.56, 1.97 and 1.98.

U.S. Pat. No. 4,166,131, issued Aug. 28, 1979 to Payne, discloses the preparation of 2,2-dialkyl-1-indanones by the cyclization of the corresponding 2,2-dialkyl-3-phenyl (or substituted phenyl) propionic acid in the presence of a mineral acid, or alternatively, the cyclization of an acid chloride of such acid with a Friedel-Crafts catalyst, e.g. aluminum chloride. Specifically disclosed is the preparation of 2,2-dimethyl-1-indanone by the cyclization of α,α-dimethyldihydrocinnamic acid using polyphosphoric acid as catalyst.

U.S. Pat. No. 3,385,895 issued May 28, 1968 to Bruson et al. discloses the preparation of β-disubstituted-α-indanones such as 2,2-dimethylindanone by reacting any of certain halogenated aliphatic ethers with carbon monoxide and an aromatic compound, e.g., benzene, in the presence of aluminum chloride or aluminum bromide. A similar process is disclosed by these patentees in Bruson et al., *J. Org. Chem.*, 32, 3356–3362 (1967), wherein a halogenated hydrocarbon such as neophyl chloride or 2-chloro-2-methyl-3-phenylpropane is reacted with benzene and carbon monoxide in the presence of aluminum chloride to yield a β-disubstituted-α-indanone such as 2,2-dimethyl-1-indanone.

Japanese Patent No. 74/10949 granted Mar. 13, 1974 to Kobayashi et al. (C. A. 82:125165g), describes the reaction of a 1,2-epoxide such as isobutylene oxide, carbon monoxide, and benzene in the presence of a Friedel-Crafts catalyst such as aluminum chloride to yield an indanone such as 2,2-dimethyl-1-indanone.

Warrick et al., *J. Am. Chem. Soc.*, 84, 4095–4100 (1962) discloses the cyclization of 2,2-dimethyl-3-phenylpropionic acid with anhydrous HF to produce 2,2-dimethyl-1-indanone.

Japanese Kokai Patent No. SHO 55 [1980]-27147, published Feb. 27, 1980, discloses the formation of aryl-substituted carboxylic acids, e.g., ibuprofen, by reacting an aryl-substituted alcohol, e.g., 1-(4'-isobutylphenyl)ethanol (IBPE), with carbon monoxide and water in the presence of a hydrogen fluoride catalyst. Also disclosed generally is the synthesis of aryl-substituted alcohols by reducing the corresponding ketones.

Czech Patent No. CS 219,752 of Sept. 15, 1985, (C. A. 104:109233v), discloses a process of making ibuprofen from isobutylbenzene including the step of reducing 4-isobutylacetophenone (IBAP) to IBPE using lithium aluminum hydride as reductant.

D. Nightingale et al., *J. Org. Chem.*, 14, 1089–1093 (1949), teach at page 1090 the hydrogenation of various aromatic ketones, including n-butyrophenone, 4-methyl-n-butyrophenone, and 2,4-dimethyl-n-butyrophenone, to produce the corresponding carbinol.

SUMMARY OF THE INVENTION

In accordance with this invention, 2,2-diorgano-1-indanones are produced by reacting an alcohol which is the corresponding (diorganosubstitutedmethyl)phenyl(or substitutedphenyl)carbinol, with carbon monoxide in the presence of a Lewis acid catalyst, with any substituents on the phenyl group of the alcohol being hydroxy or organo.

DESCRIPTION OF PREFERRED EMBODIMENTS

The reaction carried out by the inventive method process as indicated in the following equation:

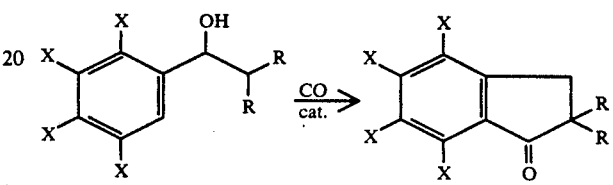

wherein the R's are organo groups which may be the same or different, with each R being preferably alkyl containing 1 to 18 carbon atoms, more preferably 1 to 4 carbon atoms, or aryl, more preferably phenyl or naphthyl, either unsubstituted, i.e., with all the ring carbon atoms bonded to hydrogen atoms, or with at least one ring carbon atom bonded to an X group other than hydrogen as hereinafter defined, and the X's are the same or different with each being hydrogen, hydroxy, $-R^1$, $-OR^1$, $-N(R^1)_2$ or $SR^1$ wherein the $R^1$'s are organo groups with each $R^1$ being preferably an alkyl group containing 1 to 18 carbon atoms, more preferably 1 to 4 carbon atoms, or an aryl group, preferably phenyl or naphthyl. As indicated in the foregoing equation a carbon atom of the benzene ring adjacent to the ring carbon atom bonded to the carbinol carbon atom in the alcohol starting material of the method herein described, must be bonded to a hydrogen atom in order for the indanone to be formed. Moreover, the benzene ring indicated in the foregoing equation could also be a naphthalene ring, with or without "X" substituents as previously defined. Most preferably, the alcohol starting compound is 2-methyl-1-phenyl-1-propanol and the product is 2,2-dimethyl-1-indanone.

The Lewis acid used as catalyst in the method of this invention may be, for example, hydrogen fluoride, polyphosphoric acid, a mixture of hydrogen fluoride and boron trifluoride, or a mixture of aluminum chloride and sodium chloride. The preferred catalyst is hydrogen fluoride.

In carrying out the reaction, the feed alcohol, carbon monoxide, and catalyst, may be charged to a corrosion-resistant reactor and the mixture maintained at a temperature, for example, of about −50° C. to about 225° C., preferably about 0° C. to 175° C., a carbon monoxide pressure of about 100 to 4000 psig, preferably about 400 to 2000 psig, for a period, for example, of about 0.1 to 24 hours, preferably about 1 to 6 hours.

If HF is used as the catalyst, it may be charged as a liquid or a gas using technologies of handling well-known to those skilled in the art. In carrying out the reaction, an inert gas such as nitrogen may be used to keep sufficient HF in contact with the reacting liquid. An excess of HF is generally used, for example, about 10 to 100 moles, preferably about 25 to about 75 moles per mole of feed alcohol initially present in the reaction zone.

The reaction may be carried out in the presence of a solvent. Preferably, however an inert solvent is employed which may be, for example, an alkane containing, e.g., about 5 to 12 carbon atoms such as n-hexane or n-octane. Other solvents suitable for use in the method of this invention include water, $C_1$–$C_4$ alcohols, chlorinated hydrocarbons, aromatic hydrocarbons, ethers, esters, and aprotic solvents such as dimethylsulfoxide. If a solvent is used, it may be present at a weight ratio of solvent to feed alcohol of about 1 to 20 preferably about 2 to 10.

The feed alcohols used to produce the 2,2-diorgano-1-indanones with the method of this invention may be made by any of various means. Preferably, however, the carbonylation reaction to produce the 1-indanone product is integrated with the production of the feed alcohol by reducing the corresponding (diorganosubstitutedmethyl)phenyl(or substitutedphenyl)ketone with a reducing agent containing available hydrogen or with hydrogen gas in the presence of a hydrogenation catalyst. The reduction proceeds as shown in the following equation where "[H]" represents the hydrogen in a hydrogen-containing reducing agent such as sodium borohydride or lithium aluminum hydride, or in hydrogen gas in the presence of a hydrogenation catalyst:

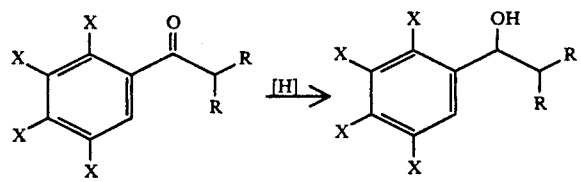

The reduction reaction shown in the foregoing equation may be accomplished, for example, by slowly adding to a cooled solution of the ketone in an alcohol, e.g., methanol, ethanol, or t-butanol, or an ether such as tetrahydrofuran or diethyl ether, a reducing agent containing available hydrogen, e.g., sodium or potassium borohydride or lithium aluminum hydride. The solution may then be warmed to room temperature and heated at reflux, e.g., for a period of about 0.5 to 3.0 hours. The reaction mixture may then be mixed with water and the product extracted with a water insoluble organic solvent, e.g., methylene chloride. The solution may then be decanted, dried with a dehydrating agent such as magnesium sulfate and concentrated in a rotary evaporator to yield the desired feed alcohol.

Alternatively, the hydrogenation or reduction as shown in the foregoing equation may be accomplished, for example, by contacting the ketone as is or dissolved in an appropriate solvent with a hydrogenation catalyst in the presence of hydrogen. The solvent may be, for example, methanol, ethanol, t-butanol, aqueous alcohol, toluene, diethyl ether, tetrahydrofuran, or 1,4-dioxane. The hydrogenation catalyst may be, for example, a transition metal or a reduced salt of such metal on a suitable support. Preferred transition metals are nickel, e.g., Raney nickel, and the noble metals, e.g., palladium, platinum, rhodium, iridium, ruthenium and osmium, and some suitable supports are, for example, carbon, alumina, silica, and polymeric resins. The metal concentration on the support in weight ratio of metal:support may be in the range, for example, of about 1:100 to 1:2, preferably about 1:50 to 1:10, and the weight ratio of catalyst system:ketone is, for example, in the range of about 1:500 to 1:2, preferably about 1:30 to 1:5. In carrying out the reaction, the hydrogen pressure may be in the range, for example, of about 10 to 1200 psig, preferably about 50 to 300 psig; the reaction temperature may be in the range, for example, of about 10° to 150° C., preferably about 20° to 80° C.; and the reaction time may be in the range, for example, of about 0.25 to 10.0 hours, preferably about 1.0 to 4.0 hours. Under some conditions, the addition of a base or passivation of the reactor with base, may be desirable to prevent hydrogenolysis.

The ketone utilized to produce the desired feed alcohol by reduction as described previously may itself be produced by various methods known in the art. For example, an aromatic compound consisting of a benzene ring containing the desired substituents, but with the ring carbon atom desired to be bonded to the keto carbon atom initially bonded to hydrogen, may be reacted in a Friedel-Crafts reaction with an appropriate acylating agent, e.g., an acid chloride, fluoride or anhydride with the desired group bonded to the carbonyl carbon atom, using a Friedel-Crafts catalyst such as hydrogen fluoride or aluminum chloride, using conditions well-known in the art.

When it is desired to produce a 1-indanone containing alkoxy substituents on the benzene ring, an aromatic ketone containing the corresponding hydroxyl groups bonded to benzene ring carbon atoms may be alkylated with an alkylating agent, e.g. dialkyl sulfate, using a suitable catalyst such as a quaternary ammonium salt. The resulting aromatic ketone containing alkoxy substituents may then be reduced to form the corresponding alcohol which in turn may then be carbonylated to form the 1-indanone, as described previously.

The following examples further illustrate the invention.

EXAMPLE 1

This example illustrates the preparation of 2,2-dimethyl-1-indanone starting with isobutyrophenone.

Sodium borohydride (6.5 g, 0.17 mol) was added in portions over a 2 h period to a solution of isobutyrophenone (50 g, 0.34 mol) in ethanol (150 mL) under nitrogen. The reaction mixture was stirred at room temperature for 2 h. Ethanol was removed under reduced pressure. The reaction mixture was added to water (100 mL) and extracted with methylene chloride (3×100 mL). The organic extract was collected, dried (anhy. $MgSO_4$), and concentrated to give 2-methyl-1-phenyl-1-propanol (48 g, 94% yield): bp 62° C. at 0.1 mm; $^1$H NMR ($CDCl_3$) 0.75 (d, J=7, 3 H), 0.96 (d, J=7, 3 H), 1.98 (m, 1 H), 2.90 (bs, 1 H), 4.25 (d, J=7, 1 H), and 7.31 (s, 5 H).

2-Methyl-1-phenyl-1-propanol (7.5 g, 0.05 mol), water (3.8 g, 0.21 mol), and hexane (32 g) were charged into a 300 cc Hastelloy C autoclave. The autoclave was purged twice with nitrogen, evacuated to 50 psig, and cooled to −30° C. Hydrogen fluoride (75.0 g, 3.25 mol) was added and the reactor was pressurized to 600 psig with carbon monoxide, heated to 50° C., and stirred for 3 h. The hydrogen fluoride was vented, and the contents were removed and poured onto crushed ice. To the mixture was added 45% potassium hydroxide solution until the pH was adjusted to 6.0–6.5. The mixture was extracted with ethyl acetate (3×100 mL). The combined organic extract was dried (anhy. MgSO4), filtered, and concentrated to give the crude product (7.6 g). The crude product was analyzed by GLC and found to contain isobutylbenzene 3.3%, 2,2-dimethyl-1-indanone 63.4%, dimer of 2-methyl-1-phenyl-1-propene 13.5%, and unidentified products about 20%.

A portion of the crude product (0.5 g) was purified by radial chromatography using 1:9 ethyl acetate/hexane. The major product was collected (0.32 g) and characterized as 2,2-dimethyl-1-indanone: IR (neat) 1717.3 cm-1; $^1$H NMR (CDCl3) 1.20 (s, 6 H), 2.95 (s, 2 H), 7.27-7.74 (m, 4 H); MS m/z 160, 145 (100), 131, 128, 117, 115, 91, 89, 65, 63, 39.

EXAMPLE 2

The carbonalyation of 2-methyl-1-phenyl-1-propanol described in Example 1 was carried out except that the reaction temperature was 30° C. and the reaction time was 1.5 h. The yield of 2,2-dimethyl-1-indanone was about 41%.

EXAMPLE 3

This example illustrates the formation of 6-methoxy-2,2-dimethyl-1-indanone starting with phenol and isobutyric anhydride.

Phenol (9.4 g, 0.1 mol) and isobutyric anhydride (15.8 g, 0.1 mol) were added to a Hastelloy C autoclave, which was checked for leaks with 60 psig nitrogen for 30 minutes and then cooled to −30° C. Anhydrous hydrogen fluoride (80 g, 4.0 mol) was added and the contents of the autoclave were warmed to 57° C. for 3 hours. The hydrogen fluoride was vented through a caustic scrubber using a nitrogen sparge. The contents of the autoclave were poured onto ice, neutralized to a pH of 7 with potassium hydroxide, and extracted with ethyl acetate (300 mL). The ethyl acetate solution was dried over anhydrous magnesium sulfate and concentrated under reduced pressure to give the crude 4-hydroxyisobutyrophenone (16.9 g). The crude product contained 90.3% p-isomer and 8.5% o-isomer by GLC analysis. The crude product was purified by vacuum distillation.

Sodium hydroxide (6.9 g, 0.17 mol) was dissolved in water (75 mL) and 4-hydroxyisobutyrophenone (25.1 g, 0.15 mol) was added to the solution. Dimethyl sulfate (22.6 g, 0.18 mol) and tetrabutylammonium iodide (0.55 g, 1.5 mmol) were added and the reaction was refluxed for 3 h. The mixture was cooled to room temperature and extracted with methylene chloride (3×150 mL). The combined organic extract was washed with water (100 mL), dried (anhy. MgSO4), filtered, and concentrated to give 4-methoxyisobutyrophenone in 77.4% purity (23.2 g, 65% yield). The crude product was purified by distillation: bp 88°-92° C. at 0.05 mm Hg.

Sodium borohydride (2.6 g, 0.069 mol) was added in portions over a 1 h period to a solution of 4-methoxyisobutyrophenone (14.6 g, 0.082 mol) in ethanol (150 mL) under nitrogen. The reaction was stirred at room temperature for 2 h. Ethanol was removed under reduced pressure. The reaction was added to water (200 mL) and acidified with 10% HCl (50 mL). The mixture was extracted with methylene chloride (3×100 mL) and the combined organic extract was collected, dried (anhy. MgSO4), and concentrated to afford 1-(4'-methoxyphenyl)-2-methyl-1-propanol in 90% purity (12.5 g, 76% yield). The crude product was purified by vacuum distillation: bp 89°-91° C. at 0.5 mm Hg.

1-(4'-Methoxyphenyl)-2-methyl-1-propanol (5.75 g, 0.032 mol), water (2.1 g, 0.13 mol), and hexane (32 g) were charged into a 300 cc Hastelloy C autoclave. The autoclave was purged twice with nitrogen, evacuated to 20 psig, and cooled to −20° C. Hydrogen fluoride (75.0 g, 3.25 mol) was added and the reactor was pressurized to 450 psig with carbon monoxide. The contents were stirred for 1 h at room temperature. The hydrogen fluoride was vented, and the contents were removed and poured onto crushed ice. To the mixture was added 45% potassium hydroxide solution until the pH was adjusted to 6.5-7.0. The mixture was extracted with ethyl acetate (3×150 mL) and the combined organic extract was dried (anhy. MgSO4), filtered, and concentrated to give the crude product (5.0 g). The crude product was analyzed by GLC and found to contain 4-methoxisobutylbenzene 19%, 6-methoxy-2,2-dimethyl-1-indanone 9%, 2,2-dimethyl-3-(4'-methoxyphenyl)-propanoic acid 6%, α-isopropyl-4-methoxybenzeneacetic acid 3%, and other unidentified products.

I claim:

1. A method for the production of 2,2-diorgano-1-indanones comprising reacting an alcohol with carbon monoxide in the presence of a Lewis acid catalyst, in accordance with the following equation:

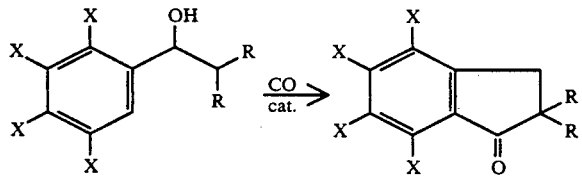

wherein the R's are the same or different with each being alkyl containing 1 to 18 carbon atoms, or phenyl or naphthyl either unsubstituted or with at least one ring carbon atom bonded to an X group other than hydrogen as hereinafter defined, and the X's are the same or different, with each being hydrogen, hydroxy —R$^1$, —OR$^1$, —N(R$^1$)$_2$ or —SR$^1$ wherein the R$^1$'s are the same or different, with each being an alkyl group containing 1 to 18 carbon atoms, phenyl or naphthyl.

2. The method of claim 1 wherein the R's are alkyl containing 1 to 4 carbon atoms and the X's are all hydrogen.

3. The method of claim 2 wherein said 1-indanone is 2,2-dimethyl-1-indanone and said alcohol is 2-methyl-1-phenyl-propanol.

4. A method for the production of 2,2-diorgano-1-indanones comprising reducing a ketone with a reducing agent containing available hydrogen or with hydrogen gas in the presence of a hydrogenation catalyst to produce an alcohol, in accordance with the following equation:

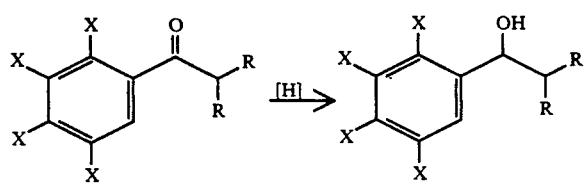

and reacting said alcohol with carbon monoxide in the presence of a Lewis acid catalyst in accordance with the following equation:

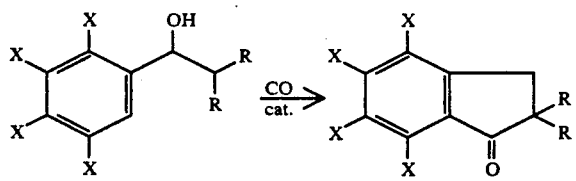

wherein the R's in the foregoing equations are the same or different with each being alkyl containing 1 to 18 carbon atoms, phenyl or naphthyl either unsubstituted or with at least one ring carbon atom bonded to an X group other than hydrogen as hereinafter defined, and the X's are the same or different, with each being hydrogen, hydroxy, $-R^1$, $-OR^1$, $-N(R^1)_2$ or $-SR^1$ wherein the $R^1$'s are the same or different with each being an alkyl group containing 1 to 18 carbon atoms, phenyl or naphthyl.

5. The method of claim 4 wherein the R's are alkyl containing 1 to 4 carbon atoms and the X's are all hydrogen.

6. The method of claim 5 wherein said 1-indanone is 2,2-dimethyl-1-indanone, said ketone is isobutyrophenone, and said alcohol is 2-methyl-1-phenyl-1-propanol.

7. The method of claim 4 wherein said reduction is carried out in the presence of a reducing agent containing available hydrogen.

8. The method of claim 1 wherein said Lewis acid is hydrogen fluoride, polyphosphoric acid, a mixture of hydrogen fluoride and boron trifluoride, or a mixture of aluminum chloride and sodium chloride.

9. The method of claim 8 wherein said reaction is carried out at a temperature of about $-50°$ C. to $225°$ C. and a carbon monoxide pressure of about 100 to 4000 psig for a period of about 0.1 to 24 hours.

10. The method of claim 7 wherein said reducing agent is sodium borohydride, potassium borohydride, or lithium aluminum hydride.

11. The method of claim 10 wherein said reduction is carried out by adding said reducing agent to a solution of said ketone in an alcohol or ether to initiate the reduction reaction and continuing the reaction for about 0.5 to 3.0 hours.

12. The method of claim 11 wherein said reaction of alcohol with carbon monoxide is carried out at a temperature of about $-50°$ C. to $225°$ C. and a carbon monoxide pressure of about 100 to 4000 psig for a period of about 0.1 to 24 hours, and said Lewis acid is hydrogen fluoride, polyphosphic acid, a mixture of hydrogen fluoride and boron trifluoride, or a mixture of aluminum chloride and sodium chloride.

13. The method of claim 4 wherein said reduction is carried out with hydrogen gas at a hydrogen pressure of about 10 to 1200 psig and a temperature of about $10°$ to $150°$ C. for a reaction time of about 0.25 to 100 hours in the presence of a hydrogenation catalyst which is nickel or a noble metal supported on carbon, alumina, silica or a polymeric resin, wherein the weight ratio of metal support is about 1:100 to 1:2 and the weight ratio of catalyst system: ketone is about 1:500 to 1:2; said reaction of alcohol with carbon monoxide is carried out at a temperature of about $-50°$ to $225°$ C. and a carbon monoxide pressure of about 100 to 4000 psig for a period of about 0.1 to 24 hours, and said Lewis acid is hydrogen fluoride, polyphosphic acid, a mixture of hydrogen fluoride and boron trifluoride, or a mixture of aluminum chloride and sodium chloride.

14. The method of claim 4 wherein said Lewis acid is hydrogen fluoride, polyphosphoric acid, a mixture of hydrogen fluoride and boron trifluoride, or a mixture of aluminum chloride and sodium chloride.

15. The method of claim 8 wherein said Lewis acid catalyst is hydrogen fluoride.

16. The method of claim 10 wherein said reducing agent is sodium borohydride.

17. The method of claim 11 wherein said Lewis acid is hydrogen fluoride.

* * * * *

UNITED STATES PATENT AND TRADEMARK OFFICE
CERTIFICATE OF CORRECTION

PATENT NO.  : 5,012,007
DATED       : April 30, 1991
INVENTOR(S) : METHOD FOR PRODUCING 1-INDANONE DERIVATIVES It is certified that error appears in the above—identified patent and that said Letters Patent is hereby corrected as shown below:

On the cover page, the following Assignee should be present:
   [73] Assignee:  HOECHST CELANESE CORPORATION
                   Somerville, New Jersey Signed and Sealed this Fifteenth Day of December, 1992

*Attest:*

DOUGLAS B. COMER

*Attesting Officer*     Acting Commissioner of Patents and Trademarks